United States Patent [19]

Omura et al.

[11] Patent Number: 4,515,930

[45] Date of Patent: May 7, 1985

[54] HIGHLY WATER-RESISTANT ADHESIVE

[75] Inventors: Ikuo Omura; Junichi Yamauchi, both of Kurashiki, Japan

[73] Assignee: Kuraray Co., Ltd., Kurashiki, Japan

[21] Appl. No.: 572,245

[22] Filed: Jan. 20, 1984

[30] Foreign Application Priority Data

Jan. 27, 1983 [JP] Japan .................................. 58-12272

[51] Int. Cl.³ ........................ A61C 5/00; C08F 130/02
[52] U.S. Cl. ..................................... 526/276; 106/35; 156/327; 156/331.2; 156/331.6; 433/224; 433/226; 433/228; 523/115; 523/116; 524/547; 526/277
[58] Field of Search ................ 526/276, 277; 433/224, 433/226, 228; 523/115, 116; 524/547; 106/35; 156/327, 331.2, 331.6

[56] References Cited

U.S. PATENT DOCUMENTS

| | | | |
|---|---|---|---|
| 3,809,685 | 5/1974 | Sato et al. | 526/277 |
| 3,884,864 | 5/1975 | Matsuda et al. | 526/277 |
| 4,044,044 | 8/1977 | Saito | 526/278 |
| 4,222,780 | 9/1980 | Shibatani et al. | 106/35 |
| 4,259,117 | 3/1981 | Yamauchi et al. | 106/35 |
| 4,277,565 | 7/1981 | Oda et al. | 526/278 |
| 4,322,509 | 3/1982 | Zalucha | 526/278 |
| 4,442,239 | 4/1984 | Tsunekawa et al. | 523/116 |
| 4,443,197 | 4/1984 | Fusayama et al. | 433/228 |

FOREIGN PATENT DOCUMENTS 0058483 9/1982 European Pat. Off. .

Primary Examiner—Ronald W. Griffin
Attorney, Agent, or Firm—Oblon, Fisher, Spivak, McClelland & Maier

[57] ABSTRACT

An adhesive which comprises (a) 1 part by weight of a polymerizable monomer represented by the formula

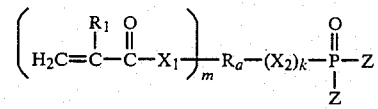

(where $R_1$ denotes H or $CH_3$; $R_a$ denotes a $C_{6-40}$ organic residue having a valence of $m+1$; $X_1$ and $X_2$ denote O, S, or NR' [where R' denotes H or a $C_{1-6}$ hydrocarbon group], two of $X_1$ may be different from each other when m is 2; Z denotes a halogen; and m is 1 or 2 and k is 0 or 1), and (b) 0 to 199 parts by weight of monomer which is copolymerizable with said monomer (a).

This adhesive firmly adheres to hard tissues of the living body such as teeth and bones, metallic materials, organic polymeric materials, and ceramics. It keeps the high adhesive strength for a long period of time under a wet condition. This adhesive is useful particularly in dentistry.

18 Claims, No Drawings

HIGHLY WATER-RESISTANT ADHESIVE

BACKGROUND OF THE INVENTION

1. Field of the Invention

This invention relates to a highly water-resistant adhesive which firmly adheres to hard tissues of the living body such as teeth and bones, metallic materials, organic polymeric materials, and ceramics. The "adhesive" as used herein not only denotes compositions used to bond adherends to one another but also comprehends compositions which are used to form a highly adhesive coating layer on the surface of adherends such as metallic materials and organic polymeric materials or used to form a highly adhesive filling material for repairing hard tissues of the living body. In other words, by "adhesive" is meant any and all compositions which are applicable for adhesion to a variety of substances including hard tissues of the living body, metallic materials, organic polymeric materials, and ceramics.

2. Description of the Prior Art

A variety of metallic materials, organic polymeric materials, and ceramic materials are in use as restorative dental materials. When in use, they are required to firmly adhere to teeth and to one another. Moreover, they are required to exhibit adhesion under a wet condition in the mouth.

Heretofore, many attempts have been made to use a phosphoric ester compound as an adhesive in dentistry. For example, U.S. Pat. Nos. 4,259,075, 4,259,117, and 4,368,043 disclose that a polymerizable composition containing a vinyl compound having a group of the formula

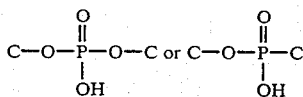

is useful as a dental adhesive. U.S. Pat. No. 4,222,780 also teaches that a polymerizable composition containing a vinyl compound having a group of the formula

is useful as a dental adhesive. In fact, some of the compositions defined in these patents have found practical use as a primer to be applied to the wall of a tooth cavity prior to the filling of a tooth cavity. The compositions disclosed in the above-mentioned patents, however, have a drawback that they do not firmly adhere to the tooth unless the surface of the tooth cavity previously undergoes acid etching. In addition, they do not firmly adhere to an Ni—Cr alloy which is a common dental metallic material.

On the other hand, attempts have been made to prepare a dental adhesive from a polymerizable phosphoric ester compound as mentioned below.

(i) U.S. Pat. No. 3,882,600 discloses phosphoryl monofluoride.

(ii) There are shown $CH_2=CH-PO(CH)_2$ and $CH_2=CHC_6H_4CH_2P-O(OH)_2$ in Journal of Dental Research, Vol. 53, p. 878–888 and Vol. 56, p. 943–952; Chemical Abstract, Vol. 77, p. 290 (66175g); and Japanese Patent Laid-open No. 44152/1976.

(iii) Japanese Patent Laid-open No. 113843/53 discloses a compound of the formula

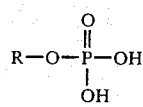

(where R is an organic residue having at least one vinyl group), with one of the two OH groups being neutralized. Said patent exemplifies the following compounds, in which M denotes a metal.

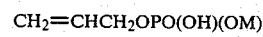

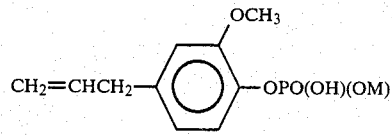

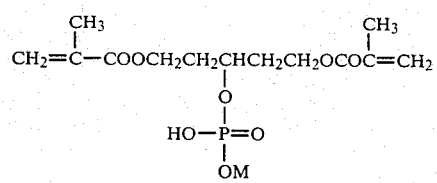

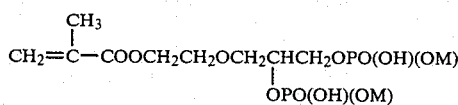

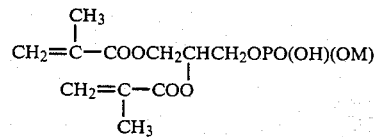

(iv) Japanese Patent Publication No. 49557/1982 teaches methacryloyloxyethane-1,1-disulfonic acid of the formula

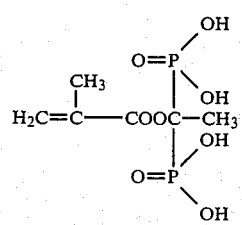

None of the compounds set forth above exhibit high adhesive strength (particularly to a metal) when used under a wet condition.

European Patent Application No. 58483 (equivalent to Japanese Patent Laid-open No. 151607/1982) describes a polymerizable monomer having a P—Cl bond or P—Br bond effective as an adhesive component. However, the compounds illustrated in this patent do not provide sufficiently high adhesive strength when applied to teeth and metallic materials.

In the industrial fields, many attempts have been made to use a phosphoric ester compound as an adhesive. For example, they are proposed in U.S. Pat. Nos. 3,754,972, 3,884,864, 3,987,127, 4,001,150, 4,044,044, and 4,223,115; Japanese Patent Laid-open No. 20238/1974, 100596/1975, 125182/1976, 12995/1978, 11920/1981, and 44638/1982; and Japanese Patent Publication Nos. 4126/1980 and 4790/1980. However, the phosphoric ester compounds described in these patents are not necessarily satisfactory in the water resistance of the adhesive strength.

SUMMARY OF THE INVENTION

It is an object of this invention to provide an adhesive composition which will find use for firmly bonding hard tissues of the living body to one another or to restorative materials (e.g., metallic, organic polymeric, and ceramic materials), or for filling the cavity of a hard tissue of the living body for restoration.

It is another object of this invention to provide an adhesive composition for industrial use and home use for bonding metallic materials to each other; bonding a metallic material to the other metallic material or an organic polymeric material or ceramic material; or bonding a ceramic material to the other ceramic material or an organic polymeric material, and to provide an adhesive composition to be used as a coating material and paint that forms a highly adhesive film on the surface of a metallic material or ceramic material.

It is further another object of this invention to provide a dental adhesive to be applied to the surface of a tooth cavity prior to the filling of the cavity in order to establish firm adhesion between the tooth and the filling material.

It is still a further object of this invention to provide a dental filling composition which firmly adheres to the tooth when used for restoring the tooth cavity.

It is an even further object of this invention to provide a dental adhesive for bonding a dental restorative material (e.g., inlay, onlay, abutment, post, bridge, splint, orthodontic bracket, and crown) to teeth, and for bonding dental restorative materials to each other (e.g., bonding abutment to crown).

It is an additional object of this invention to provide a dental adhesive to be used as a pit and fissure sealant which is applied to the tooth surface to prevent tooth decay.

It is a further additional object of this invention to provide a method for performing complete restoration of teeth by firmly bonding a filling material to a tooth and by firmly bonding restorative materials to each other, and a method for coating the tooth surface for the prevention of tooth decay.

The above-mentioned objects of this invention are achieved by an adhesive which comprises (a) 1 part by weight of polymerizable monomer represented by the formula

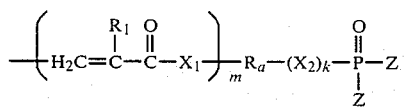
(I)

(where $R_1$ denotes H or $CH_3$; $R_a$ denotes a $C_{6\text{-}40}$ organic residue having a valence of m+1; $X_1$ and $X_2$ denote O, S, or NR' [where R' denotes H or a $C_{1\text{-}6}$ hydrocarbon group], two of $X_1$ may be different from each other when m is 2; Z denotes a halogen (F, Cl, Br, and I); and m is 1 or 2 and k is 0 or 1), and (b) 0 to 199 parts by weight of monomer which is copolymerizable with said monomer (a).

DETAILED DESCRIPTION OF THE INVENTION

The adhesive of this invention is characterized in that the above-mentioned compound (I) is used as a monomer that, on polymerization, imparts adhesive properties. (This monomer may be referred to as adhesive monomer.)

As compared with the adhesive monomer exemplified in the above-mentioned Japanese Patent Laid-open No. 151607/1982, the adhesive monomer of the adhesive of this invention has $R_a$ of higher carbon number. This Japanese Patent does not mention that the adhesive strength is greatly affected by the carbon number of the organic residue connecting the polymerizable group having a double bond and the $-POCl_2$ or $-POBr_2$ group, whereas the present inventors unexpectedly found that as the carbon number of $R_a$ is increased, the resulting adhesive firmly adheres to not only teeth, but also metallic and ceramic materials.

The term "organic residue" as used herein denotes an organic residue made up of a carbon skeleton which may have a hetero atom (O, S, N, or P). Preferred ones have the following structural features (i) and (ii).

(i) A hydrocarbon group which may have an OH group, COOH group, or halogen (F, Cl, Br, or I) as a substituent group.

(ii) An organic residue of carbon number 6 to 30 in which 2 to 7 hydrocarbon groups (each having 1 to 29 carbon atoms and at least one having 3 or more carbon atoms), which may have the above-mentioned substituent group, are connected to one another through a linkage of the type selected from the group consisting of

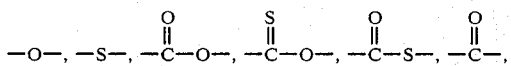

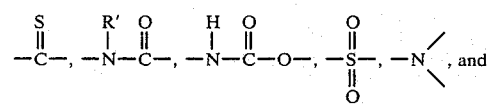

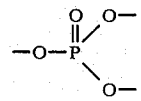

(where R' denotes H or a $C_{1\text{-}6}$ hydrocarbon group).

The organic residue having the above structure (ii) includes one in which the main chain is made up of a plurality of hydrocarbon groups and a part of the hydrocarbon groups constitutes the side chain of the skeleton. Illustrated below are the hydrocarbon groups (represented by A) connected through the linkage (represented by B). For simplicity, the group having the double bond is expressed by [C=C] and the group of oxyhalogenated phosphorus is expressed by [P].

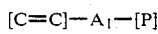

-continued $$[C=C]-A_1-B_1-A_2-B_2-A_3-[C=C]$$
$$\phantom{[C=C]-A_1-B_1-A_2-}|\phantom{-A_2-A_3-[C=C]}$$
$$\phantom{[C=C]-A_1-B_1-A_2-}[P]$$

$$[C=C]-A_1-B_1-A_2-[P]$$
$$\phantom{[C=C]-A_1-}|$$
$$\phantom{[C=C]-A_1-}A_3$$

$$[C=C]-A_1-B_1-A_2-B_2-A_3-[P]$$
$$\phantom{[C=C]-A_1-B_1-A_2-}|$$
$$\phantom{[C=C]-A_1-B_1-A_2-}B_3$$
$$\phantom{[C=C]-A_1-B_1-A_2-}|$$
$$\phantom{[C=C]-A_1-B_1-A_2-}A_4$$

$$\begin{matrix}[C=C]\\ \phantom{[}\diagdown\\ [C=C]\end{matrix} A_1-B_1-A_2-[P]$$
with $A_3$, $B_2$, $A_4$ branches $$[C=C]-A_1-B_1-A_2-B_2-A_3-[P]$$
with $A_4$, $B_3$, $B_4$, $A_5$ branches The term "hydrocarbon group" as used in this invention comprehends halogenated hydrocarbon groups, unless otherwise noted.

The above-mentioned compound (I) exhibits the highest adhesive strength and firmly adheres to teeth, metallic materials, and ceramic materials when m is 1, $X_1$ and $X_2$ are —O—, and $R_a$ is:

$-(CH_2)_n-$   [where n is a natural number from 6 to 20.]   (i)

$-CH_2-\langle\text{phenyl}\rangle-CH_2-$ , $-CH_2-\langle\text{H cyclohexyl}\rangle-CH_2-$ , (ii)

or $-CH_2CH_2CHCH_2CH_2-$
$\phantom{or -CH_2CH_2}|$
$\phantom{or -CH_2CH_2}CH_3$ $-(CH_2)_l-O-\langle\text{phenyl}\rangle-O-(CH_2)_l-$   [where l is 2, 3, or 4.]   (iii)

$-CH_2CH-$   (iv)
$\phantom{-CH_2}|$
$\phantom{-CH_2}CH_2O(CO)_p-R_b$

[where p is 0 or 1, and $R_b$ is a $C_{3-16}$ hydrocarbon group.]

Examples of the adhesive monomer used in this invention are shown below.

$$H_2C=\underset{CH_3}{\overset{|}{C}}-COO(CH_2)_6-O-\underset{Cl}{\overset{O}{\underset{\|}{P}}}-Cl$$

$$H_2C=\underset{CH_3}{\overset{|}{C}}-COO-(CH_2)_8-O-\underset{Br}{\overset{O}{\underset{\|}{P}}}-Br$$

$$H_2C=\underset{CH_3}{\overset{|}{C}}-COO-(CH_2)_{10}-O-\underset{Cl}{\overset{O}{\underset{\|}{P}}}-Cl$$

$$H_2C=\underset{CH_3}{\overset{|}{C}}-COO-(CH_2)_{20}-O-\underset{Cl}{\overset{O}{\underset{\|}{P}}}-Cl$$

$$H_2C=\underset{H}{\overset{|}{C}}-COO-(CH_2)_{40}-O-\underset{Cl}{\overset{O}{\underset{\|}{P}}}-Cl$$

$$H_2C=\underset{CH_3}{\overset{|}{C}}-COO-(CH_2)_{10}-O-\underset{F}{\overset{O}{\underset{\|}{P}}}-F$$

$$H_2C=\underset{CH_3}{\overset{|}{C}}-COOCH_2CH_2\underset{CH_3}{\overset{|}{C}H}CH_2CH_2-O-\underset{F}{\overset{O}{\underset{\|}{P}}}-F$$

$$H_2C=\underset{CH_3}{\overset{|}{C}}-COOCH_2-\langle\text{H}\rangle-CH_2-O-\underset{Cl}{\overset{O}{\underset{\|}{P}}}-Cl$$

$$H_2C=\underset{CH_3}{\overset{|}{C}}-COOCH_2CH_2OCH_2C\equiv CCH_2OCH_2CH_2-O-\underset{I}{\overset{O}{\underset{\|}{P}}}-I$$

$$H_2C=\underset{CH_3}{\overset{|}{C}}-COOCH_2-\langle\text{phenyl}\rangle-CH_2-O-\underset{Cl}{\overset{O}{\underset{\|}{P}}}-Cl$$

$$H_2C=\underset{CH_3}{\overset{|}{C}}-COOCH_2CH_2O-\langle\text{phenyl}\rangle-OCH_2CH_2-O-\underset{Cl}{\overset{O}{\underset{\|}{P}}}-Cl$$

$$H_2C=\underset{CH_3}{\overset{|}{C}}-COO-(CH_2)_4O-\langle\text{phenyl}\rangle-O-(CH_2)_4O-\underset{Cl}{\overset{O}{\underset{\|}{P}}}-Cl$$

$$H_2C=\underset{CH_3}{\overset{|}{C}}-COOCH_2\underset{CH_2CH_3}{\overset{CH_2OH}{\overset{|}{C}}}-CH_2-O-\underset{Cl}{\overset{O}{\underset{\|}{P}}}-Cl$$

$$H_2C=\underset{CH_3}{\overset{|}{C}}-COOCH_2CH_2O\overset{O}{\overset{\|}{C}}NH-\langle\text{phenyl-Cl}\rangle-NH\overset{O}{\overset{\|}{C}}OCH_2CH_2-O-\underset{Cl}{\overset{O}{\underset{\|}{P}}}-Cl$$

$$H_2C=\underset{CH_3}{\overset{|}{C}}-COOCH_2\underset{(CH_2)_7CH_3}{\overset{|}{C}H}-O-\underset{Cl}{\overset{O}{\underset{\|}{P}}}\diagdown\overset{Cl}{\phantom{|}}$$

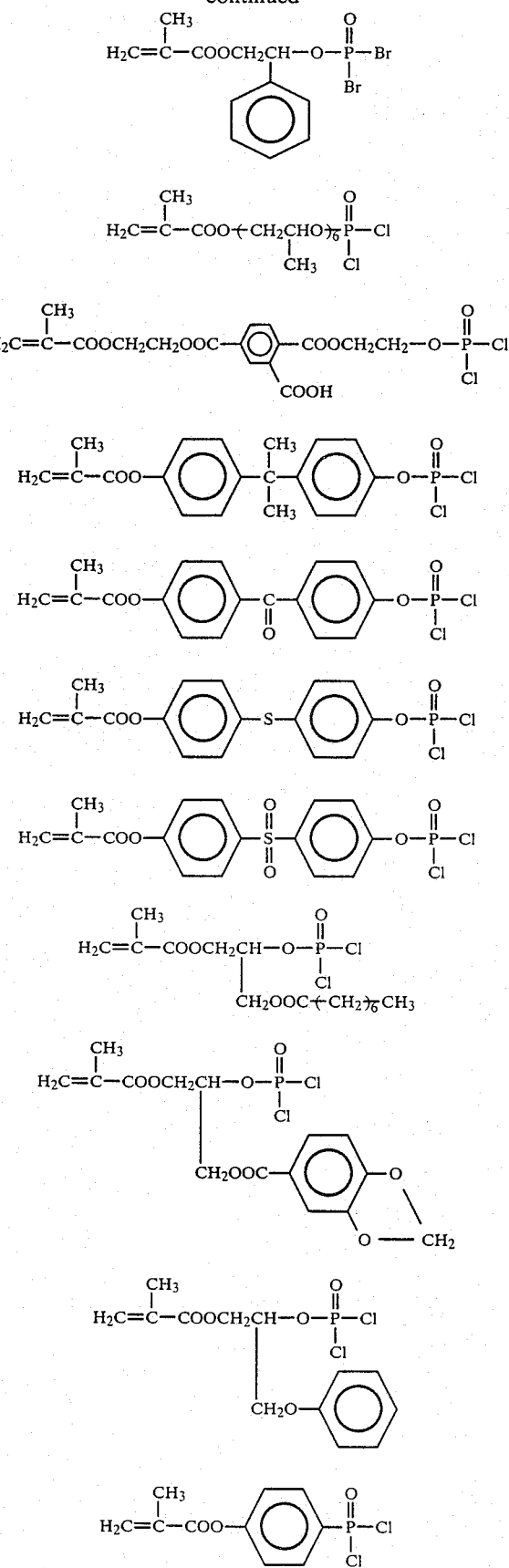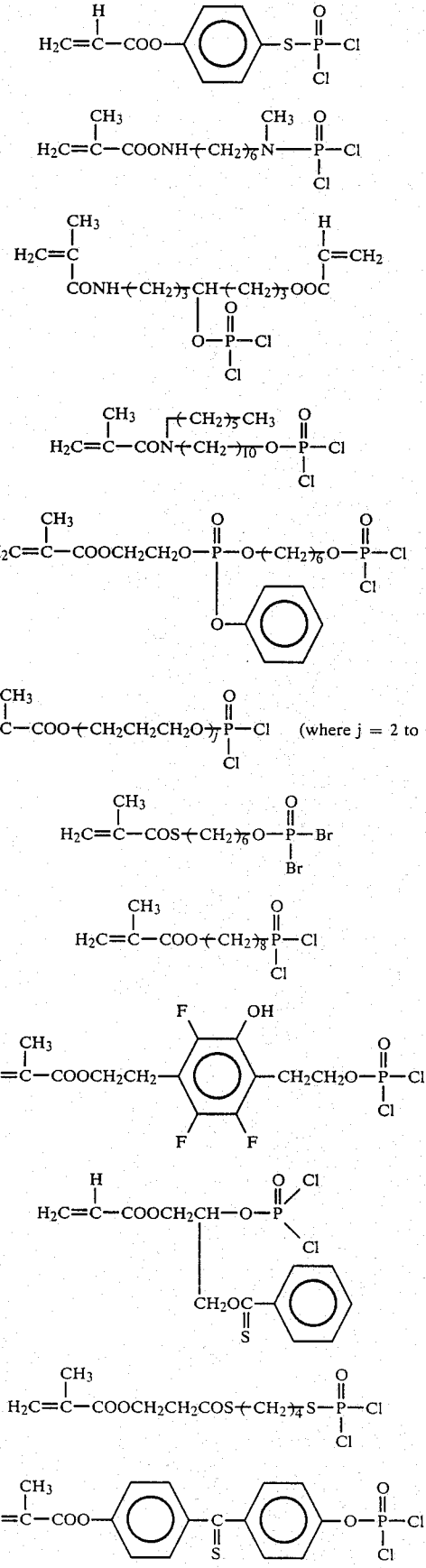

-continued

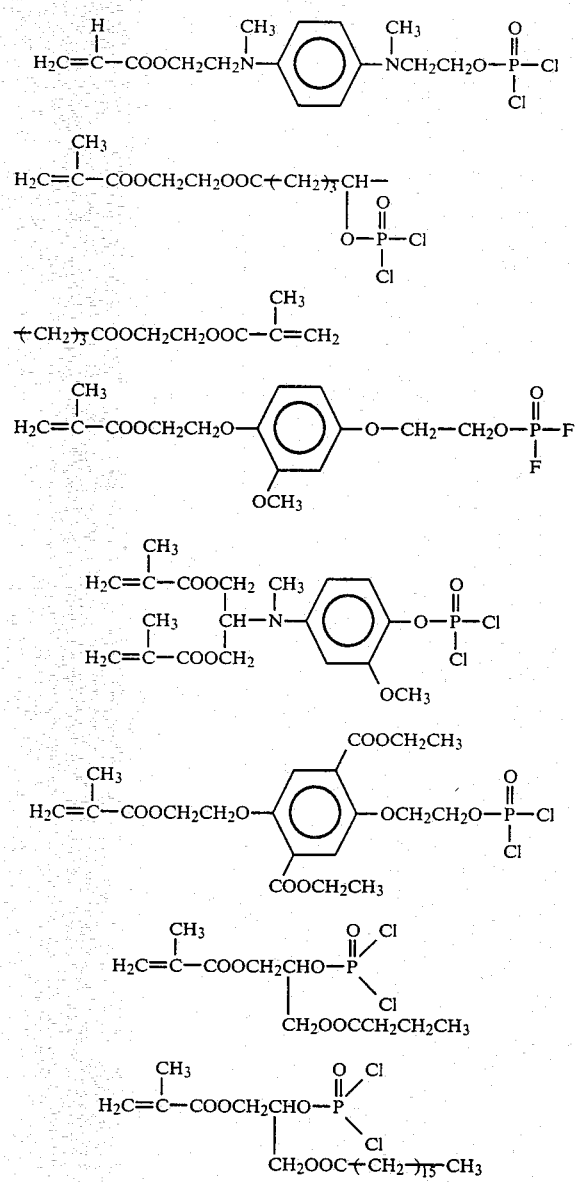

In the case where $R_a$ in the compound of formula (I) has a carbon number of 4 or less, the resulting adhesive is extremely poor in adhesion to teeth, metallic materials, and ceramic materials and is also poor in water resistance of adhesive strength, as compared with the adhesive of this invention. In general, there is a tendency that as the carbon number of $R_a$ increases, the resulting adhesive increases in adhesive strength. When $R_a$ has the carbon number 6, the object of this invention is achieved; and when $R_a$ has the carbon number 8 to 20, the adhesive exhibits the highest adhesive strength. As the carbon number of $R_a$ increases more than 30, the resulting adhesive becomes poor in adhesive strength. Therefore, it is necessary that the carbon number of $R_a$ should be less than 40, if the object of this invention is to be achieved.

The adhesive of this invention is formed by mixing the compound of formula (I) with a vinyl monomer which is copolymerizable with the compound. The copolymerizable monomer affects the viscosity, wettability, curability, and mechanical properties of the adhesive. Thus it should be properly selected according to the intended use of the adhesive. Usually, it is meth(acrylate) type monomer, styrene type monomer, or vinyl acetate. The monomer is not limited to them, however. It also includes (meth)acrylamide, N-n-butoxymethyl(meth)acrylamide, N(hydroxymethyl)acrylamide, and other acrylamides; and (meth)acrylic acid, isobutylvinyl ether, diethyl fumarate, diethyl maleate, maleic anhydride, methyl vinyl ketone, allyl chloride, vinyl naphthalene, and vinylpyridine. The above-mentioned styrene type monomer includes those compounds (such as divinyl benzene and p-chlorostyrene) represented by

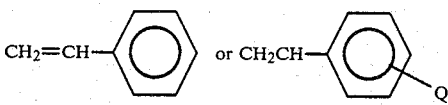

(where Q denotes a halogen or a $C_{1-6}$ hydrocarbon group). The (meth)acrylate type monomer is one which is commonly used for anaerobic adhesives and dental adhesives. It is a (meth)acrylate monomer represented by

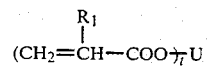

(where $R_1$ denotes H or $CH_3$, U denotes a $C_{1-50}$ organic group, t denotes an integer of 1 to 4, and the organic group is defined above). Examples of such monomer include the following.

(i) Monofunctional (meth)acrylate

Methyl (meth)acrylate, ethyl (meth)acrylate, n-butyl (meth)acrylate, iso-butyl (meth)acrylate, n-hexyl (meth)acrylate, 2-ethylhexyl (meth)acrylate, benzyl (meth)acrylate, decyl (meth)acrylate, lauryl (meth)acrylate, stearyl (meth)acrylate, 2-hydroxyethyl (meth)acrylate (HEMA), 2-hydroxypropyl (meth)acrylate, dimethylaminoethyl (meth)acrylate, diethylaminoethyl (meth)acrylate, 3-chloro-2-hydroxypropyl methacrylate, and 2,3-dibromopropyl (meth)acrylate.

(ii) Difunctional (meth)acrylate (a) One is which U is $-CH_2CH_2(OCH_2CH_2)_s-$ or $$-CH_2CH(OCH_2CH)_s-$$
$$\phantom{-CH_2CH(O}CH_3\phantom{CH_2CH)_s}CH_3$$

(where s is an integer of 0 to 15).

Ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, and tripropylene glycol di(meth)acrylate.

(b) One in which U is an alkylene of carbon number 3 to 12

Propanediol di(meth)acrylate, glycerin di(meth)acrylate, 1,3-butanediol di(meth)acrylate, 1,4-butanediol di(meth)acrylate, 1,5-pentanediol di(meth)acrylate, 1,6-hexanediol di(meth)acrylate, neopentylglycol di(meth)acrylate, 1,10-decanediol di(meth)acrylate, and 2,3-dibromoneopentyl glycol dimethacrylate.

(c) On in which U has a residue of bisphenol-A derivative

Bisphenol-A di(meth)acrylate, 2,2-bis[(meth)acryloyloxy polyethoxyphenyl]propane,

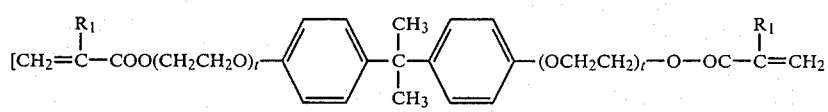

where t is an integer of 1 to 9], 2,2'-bis(4-acryloyloxy propoxyphenyl)propane, and 2,2-bis[4-(3-methacryloyloxy-2-hydroxypropoxy)phenyl]propane (Bis-GMA). Preferable among them are those in which U has a carbon number 15 to 30.

(d) One in which U is

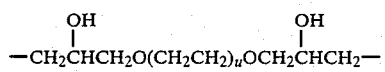

(where u is 1 or 2)
1,2-bis[3-(meth)acryloyloxy-2-hydroxypropoxy]ethane, and 1,4-bis[3-(meth)acryloyloxy-2-hydroxypropoxy]butane.

(e) One in which U is JOCONHTNHCOOJ [where J denotes a $C_{2-10}$ alkylene, and T denotes an organic diisocyanate residue of carbon number 1 to 50]

Urethane di(meth)acrylate, as disclosed in Japanese Patent Laid-open No. 687/1975.

(iii) Tri- and tetrafunctional methacrylates

Trimethylolpropane tri(meth)acrylate, trimethylolethane tri(meth)acrylate, tetramethylolmethane tetra(meth)acrylate, and N,N'-(2,2,4-trimethylhexamethylene)bis[2-(aminocarboxy)propane-1,3-diol]tetramethacrylate.

The above-mentioned copolymerizable monomers are used individually or in combination with one another. The most preferred one for dental adhesive is methacrylate ester, and it should preferably account for more than 50 wt% of the total copolymerizable monomer. Preferred examples of methacrylate ester include methyl methacrylate, ethyl methacrylate, HEMA, n-hexyl methacrylate, benzyl methacrylate, lauryl methacrylate, bis-GMA, bisphenol-A dimethacrylate, 2,2-bis[(meth)acryloyloxy polyethoxyphenyl]propane, ethylene glycol dimethacrylate, diethylene glycol dimethacrylate, triethylene glycol dimethacrylate, 1,6-hexanediol dimethacrylate, 1,10-decanediol dimethacrylate, neopentyl glycol dimethacrylate, and trimethylolethane trimethacrylate.

In the adhesive of this invention, the compound of formula (I) should be contained more than 0.5 wt% in the total polymerizable monomer; in other words, the above-mentioned copolymerizable monomer should be used in an amount of 0 to 199 parts by weight for 1 part by weight of the compound of formula (I). If the content of the compound of formula (I) is less than 0.5 wt%, the resulting adhesive is insufficient in adhesive strength. The compound of formula (I) should preferably be used more than 1.5 wt%.

The adhesive of this invention exhibits its adhesive strength when polymerized and cured after application to the adherend or filling into the cavity. The curing is accomplished physically with heating or irradiation of X-rays, ultraviolet rays, or visible light, or chemically with a polymerization initiator. Usually, the adhesive is incorporated with a photosensitizer or a polymerization initiator to facilitate curing. They are collectively called a curing agent in this invention. The curing agent that can be used in this invention includes organic peroxides, azo compounds, organometallic compounds, redox initiators, and photosensitizers for ultraviolet rays and visible light. Examples include benzoyl peroxide, di-t-butyl peroxide, cumene hydroperoxide, t-butylhydroperoxide, methyl ethyl ketone peroxide, azobisisobutyronitrile, organic sulfinic acid (or salt thereof), tributyl borane, hydrogen peroxide/$Fe^{2+}$ salt, cumene hydroperoxide/$Fe^{2+}$ salt, benzoyl peroxide/N,N-dialkylaniline derivative, ascorbic acid/$Cu^{2+}$ salt, organic sulfinic acid (or salt thereof)/amine (or salt thereof)/peroxide, α-diketone/allylthiourea (visible light curing), benzoin methyl ether, benzoinethyl ether, benzyl, diacetyl, diphenyldisulfide, and di-β-naphthyl sulfide. Preferable among them are benzoyl peroxide, azobisisobutyronitrile, tributyl borane, and organic sulfinic acid (or salt thereof)/diacyl peroxide/aromatic secondary or tertiary amine (or salt thereof). The aromatic sulfinic acid includes benzenesulfinic acid, p-toluenesulfinic acid, β-naphthalenesulfinic acid, and styrenesulfinic acid. The cation which forms a salt with the sulfinic acid is an alkali metal ion, alkaline earth metal ion, or ammonium ion. The former two are preferred from the standpoint of storage stability and adhesive strength. Their examples are $Li^+$, $Na^+$, $K^+$, $Mg^{2+}$, $Ca^{2+}$, and $Sr^{2+}$. The preferred examples of aromatic amines include N,N-dimethylaniline, N,N-dimethyl-p-toluidine, N-N-diethanolaniline, N,N-diethanol-p-toluidine, N-methylaniline, and N-methyl-p-toluidine. These amines may form a salt with hydrochloric acid, acetic acid, or phosphoric acid. The diacyl peroxide includes benzoyl peroxide, m-toluoylperoxide, 2,4-dichlorobenzoyl peroxide, octanoyl peroxide, lauroyl peroxide, and succinic acid peroxide. Preferable among them are benzoyl peroxide and m-toluoyl peroxide. These curing agents are added in an amount of 0.01 to 20 parts by weight, preferably 0.1 to 15 parts by weight, for 100 parts by weight of the polymerizable monomer.

In some cases, it is desirable to incorporate the adhesive of this invention with a volatile organic solvent having a boiling point lower than 150° C. at 760 Torr. Such an embodiment is preferable where the adhesive of this invention is used as a primer to be applied to the tooth cavity prior to the filling of a dental filling material. After application, the volatile organic solvent is vaporized by blowing air or nitrogen so that a film of the adhesive is formed on the adherend. The preferred organic solvent includes methanol, ethanol, acetone, methyl ethyl ketone, methyl acetate, ethyl acetate, dichloromethane, chloroform, ethyl ether, isopropyl ether, and toluene. The volatile organic solvent is used in an amount of less than 300 times (by weight), preferably less than 100 times, the weight of the total polymerizable monomer. Dilution in excess of 300 times results in a great decrease in adhesive strength due to an excessively thin film of polymerizable monomer formed after the volatilization of the solvent.

The adhesive of this invention may be incorporated with a known filler (inorganic, organic polymer, or inorganic-organic composite type). When incorporated with a filler, the adhesive of this invention can be used as a dental cement (for adhesion and filling), dental composite resin, and bone cement. The filler should be added in an amount of less than 1000 parts by weight, preferably 20 to 500 parts by weight, for 100 parts by weight of the polymerizable monomer. The filler improves the rheological properties of the adhesive composition at the time of its use, the mechanical properties of the cured adhesive, and the adhesive strength and the resistance of the adhesive strength to water. Examples of the inorganic filler include natural minerals such as quartz, felstone, pottery stone, wallastonite, mica, clay, kaolin, and marble; ceramics such as silica, alumina, silicon nitride, boron carbide, boron nitride, soda glass, barium glass, strontium glass, borosilicate glass, and lanthanum-containing glass ceramic; and water-insoluble inorganic salts such as barium sulfate and calcium carbonate. Usually, the inorganic filler undergoes surface treatment with a silane coupling agent such as γ-methacryloyloxypropyl trimethoxy silane, vinyl trimethoxy silane, vinyl triethoxy silane, vinyl trichlorosilane, vinyl tris(2-methoxyethoxy)silane, vinyl triacetoxy silane, and γ-mercaptopropyl trimethoxy silane. The organic polymeric filler includes polymethyl methacrylate, polyamide, polyester, polypeptide, polysulfone, polycarbonate, polystyrene, chloroprene rubber, nitrile rubber, styrene-butadiene rubber, and polyvinyl acetate. The inorganic-organic composite type filler includes the silane-treated inorganic filler coated with the above-mentioned polymer.

These fillers are used individually or in combination with one another. The filler may be of formless, spherical, lamellar, or fibrous, having a particle diameter smaller than 100 microns. The polymeric filler may be dissolved in the polymerizable monomer or a volatile organic solvent. Inorganic fillers and inorganic-organic composite type fillers are preferable where the adhesive of this invention is used as a dental cement or dental composite resin, and organic fillers are preferable where it is used as a bone cement.

In the case where the adhesive of this invention is intended for industrial use and home use, the adhesive may be incorporated with an organic solvent-soluble polymer such as PMMA, polystyrene, polyvinyl acetate, chloroprene rubber, butadiene rubber, nitrile rubber, and chlorosulfonated polyethylene in an amount of less than 200 parts by weight, preferably less than 120 parts by weight, for 100 parts by weight of the vinyl monomer composition, whereby the adhesive is increased in viscosity and the mechanical properties of the cured adhesive are improved.

In addition to the above-mentioned additives, the adhesive of this invention may be incorporated with a polymerization inhibitor [e.g., hydroquinone methyl ether (MEHQ)], antioxidant [e.g., 2,6-di-tert-butyl-p-cresol (BHT)], ultraviolet absorbing agent, pigment, phthalic acid diester, silicone oil, etc., as occasion demands, according to the performance required. These additives are added in an amount of less than 10 parts by weight, preferably less than 5 parts by weight, for 100 parts by weight of the polymerizable monomers.

In the case where the adhesive of this invention is used in dentistry and orthopedics, a redox initiator of room temperature curing type is commonly used. In such a case, the oxidizing agent and the reducing agent should be packed separately to ensure storage stability, and a special attention should be paid to the package form. Examples of the package form include the two-pack systems, each pack containing vinyl compound plus reducing agent and vinyl compound plus oxidizing agent; vinyl compound plus oxidizing agent (or reducing agent) and volatile organic solvent plus reducing agent (or oxidizing agent); vinyl compound plus oxidizing agent (or reducing agent) and filler plus reducing agent (or oxidizing agent); or vinyl compound plus filler plus oxidizing agent and vinyl compound plus filler plus reducing agent. In the case of the three-component system composed of organic sulfinic acid (or salt thereof)/amine (or salt thereof)/peroxide, which is most suitable for the adhesive of this invention, the sulfinic acid and amine function as the reducing agent and the peroxide as the oxidizing agent. In this case, a three-pack system may be employed in which the sulfinic acid and amine are separated from each other.

In the case where a photosensitizer is used as a curing agent, the package containing the vinyl compound and photosensitizer should be stored in a container shielded against light. In the case where an initiator (such as tributyl borane) is employed which initiates polymerization in a short time on contact with the vinyl compound, the initiator and the vinyl compound should be packed separately from each other. The two-pack adhesive composition is mixed together immediately before use.

The adhesive of this inventon, which keeps high adhesive strength under wet conditions over long periods of time, exhibits outstanding adhesion for the following materials:

(i) Hard tissues of the living body, such as teeth and bones.

(ii) Base metals and alloys thereof such as iron, nickel, chromium, cobalt, aluminum, copper, zinc, tin, stainless steel, and brass; and noble metal alloys containing 50 to 90% of gold or platinum, which are difficult to bond with a conventional adhesive.

(iii) Ceramics such as glass, porcelain, silica, and alumina.

(iv) Organic polymers such as polymethyl methacrylate, polyester, polyamide, polyurethane, polycarbonate, polysulfone, and polystyrene.

Because of its ability to exhibit high adhesive strength for a variety of materials as mentioned above, the adhesive of this invention will find use in various application areas. Examples of preferred applications are as follows:

(i) Dentistry

The adhesive is applied to the wall of a tooth cavity to be filled with a composite resin which is usually composed of a polymerizable monomer, filler, and polymerization initiator. When supplied to the dentist, the adhesive is combined with the composite resin to form a system.

The adhesive composition incorporated with a filler is used as a composite resin to be filled in the tooth cavity. Not only does the adhesive composition function as a filling material but also it firmly adheres to the tooth.

The adhesive is used to bond an inlay, onlay, or abutment to a tooth cavity; to fasten a bridge, post, splint, or orthodontic bracket to teeth; or to bond a crown to an abutment.

The adhesive is used as a pit and fissure sealant.

For each application, the specific composition of the adhesive is selected as mentioned above. For example, if the adhesive is to be coated on a tooth prior to the filling of a composite resin, the adhesive composition may be prepared according to the recipe as shown in U.S. Pat. Nos. 4,259,075 and 4,259,117. That is, the adhesive composition is made up of 1.5 to 100 wt% of the above-mentioned vinyl compound (which exhibits adhesion on polymerization), a polymerizable monomer (such as bis-GMA, HEMA, and aliphatic dimethacrylate), an organic solvent (such as ethanol) as a diluent, and a curing agent of room temperature curing type. Also, if the adhesive composition is to be used in the form of a composite resin, it is prepared according to the recipe shown in the above-mentioned U.S. Patents. That is, the above-mentioned adhesive vinyl compound is added in an amount of 1.5 to 50 wt% (based on the total polymerizable monomers) to a conventional filler material composed of 20 to 40 wt% of polymerizable monomer (such as bis-GMA) and 80 to 60 wt% of filler.

The adhesive thus prepared is applied to a tooth in the usual way. On curing, the composite resin adheres to a tooth so firmly that it is not necessary to provide mechanical retention such as undercut. (It is preferable to subject the tooth surface to acid etching before the adhesive of this invention is applied to the tooth; however, it provides practically sufficient adhesive strength without acid etching, unlike the compositions disclosed in U.S. Pat. Nos. 4,259,075 and 4,259,117. There is some fear for the injurious effect of acid etching on the dentin.)

The adhesive composition to bond an inlay, onlay, or crown to a tooth cavity or abutment should preferably be composed of 1.5 to 50 parts by weight of the adhesive vinyl monomer, 98.5 to 50 parts by weight of the copolymerizable monomer, and 50 to 500 parts by weight of filler. With the adhesive composition thus prepared, it is possible to achieve the bonding of an inlay, onlay, or crown to a tooth cavity, which could not be achieved with a conventional luting cement.

In an additional application in dentistry, a liquid composed of the adhesive vinyl monomer, copolymerizable monomer, and curing agent is applied to the tooth surface, followed by curing, so that the firmly-bonding film formed on the tooth surface prevents tooth decay.

(ii) Orthopedics

The adhesive composition of this invention will find use as a bone cement to bond a ceramic or metallic artificial joint or splint to a bone. The adhesive composition for such use should preferably be composed of 90 to 98.5 parts by weight of methyl methacrylate, 10 to 1.5 parts by weight of adhesive vinyl monomer, and 50 to 150 parts by weight of filler(e.g., PMMA).

(iii) General industrial and home uses

Because of its outstanding adhesion to metals, ceramics, and organic polymers, the adhesive of this invention will find general use in the areas of transport, electric machines, building materials, can manufacture, ceramic industry, and home appliances. It will also find use as a coating material such as a paint and an undercoating. When used for coating, it adheres much more firmly to the substrate than the existing adhesive of polymerization curing type (such as cyanoacrylate, epoxy resin, and second-generation acrylic adhesive), even if the substrate is stained with oil or wetted. This is a surprising feature of the adhesive of this invention.

Having generally described the invention, a more complete understanding can be obtained by reference to certain specific examples, which are intended for purpose of illustration only and are not intended to be limiting.

PRODUCTION EXAMPLE 1

The adhesive monomer used in this invention was prepared as follows: Into a 200-cc three-neck flask were charged 56 g of methacrylic acid, 76 g of 1,6-hexanediol, 6 g of p-toluenesulfonic acid, and 0.2 g of MEHQ. The reactants were heated to 85° C. under reduced pressure (170 mmHg), and the reaction was carried out for several hours, while blowing oxygen, until water was not distilled any longer. The reaction liquid was cooled to room temperature and then transferred to a separatory funnel. The reaction liquid was washed with 5% aqueous solution of sodium carbonate until the washings became alkaline. The reaction liquid was further washed with five 100 cc portions of neutral water. After dehydration with anhydrous sodium sulfate, the reaction liquid, with 12 mg of MEHQ added, was heated to 80° C. under reduced pressure to remove the residual water. Thus there was obtained 74 g of a mixture of 1,6-hexanediol monomethacrylate and 1,6-hexanediol dimethacrylate. The analysis by high-performance liquid chromatography (HLC) showed that the content of monoester was 75 mol% and the residual quantity of feedstock diol was less than 0.5 wt%.

Into a 500 cc reactor was charged 22.9 g of phosphorus oxychloride dissolved in 100 cc of ethyl ether, followed by cooling to $-50°$ C. 40.5 g of the previously prepared methacrylic ester mixture and 15.4 g of triethylamine, both dissolved in 100 cc of ethyl ether, were added slowly dropwise, through a 200 cc dropping funnel connected to the reactor, to the phosphorus oxychloride solution, with vigorous stirring, while blowing dry nitrogen. After addition was complete, the reaction liquid was kept at $-30°$ C. for 3 hours, and then the reaction liquid was warmed to room temperature. The triethylamine hydrochloride which had separated out was filtered off by a glass filter. To the filtrate was added 40 mg of MEHQ and the ethyl ether was distilled away under reduced pressure to give nonvolatile liquid residue. Dimethacrylate in the residue was extracted out with four 200 cc portions of n-hexane, and then residual n-hexane in the residue was distilled away under reduced pressure. Thus there was obtained 32 g of oily substance. It was confirmed by elemental analyses and $H^1$- and $P^{31}$-NMR that the oily substance is a compound of the following formula:

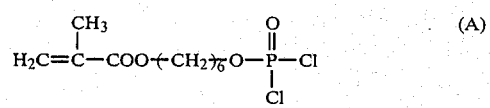

(A)

PRODUCTION EXAMPLE 2

The adhesive monomer used in this invention was prepared as follows: Into a 500-cc three-neck flask were charged 56 g of methacrylic acid, 92 g of 1,10-decanediol, 6 g of p-toluenesulfonic acid, and 0.2 g of MEHQ. The reactants were heated to 80° C. to make a uniform solution. The flask was evacuated to 150 mmHg, and the esterification reaction was carried out at 90° C. while blowing oxygen with stirring. The reaction was ceased when water was not distilled away any longer. After cooling to room temperature, the reaction liquid was diluted with 150 cc of n-hexane. The solids which separated out on dilution were filtered off, and the filtrate was washed with an aqueous solution of sodium carbonate until the washings became alkaline. After repeated washing with water, the reaction liquid was diluted with 500 cc of n-hexane. The reaction liquid was allowed to stand at 5° C. with anhydrous sodium sulfate added thereto. One day later, the unreacted diol which had separated out during standing was filtered off again. The filtrate, with 10 mg of MEHQ added, was heated to 80° C. under reduced pressure to remove n-hexane. Thus there was obtained 110 g of a mixture of methacrylate monoester and diester of 1,10-decanediol. The analysis by HLC showed that the content of monoester was 65 mol% and only a trace of unreacted diol was contained.

Into a 500 cc reactor was charged 22.9 g of phosphorus oxychloride dissolved in 100 cc of ethyl ether, followed by cooling to −50° C. 61.5 g of the previously prepared ester mixture and 15.4 g of triethylamine, both dissolved in 120 cc of ethyl ether, were added slowly dropwise, through a 300 cc dropping funnel connected to the reactor, to the phosphorus oxychloride solution, with vigorous stirring, while blowing dry nitrogen. After addition was complete, the reaction liquid was kept at −30° C. for 3 hours, and then the reaction liquid was warmed to room temperature. The triethylamine hydrochloride which had separated out was filtered off by a glass filter. To the filtrate was added 40 mg of MEHQ and the ethyl ether was distilled away under reduced pressure to give nonvolatile liquid residue. Dimethacrylate in the residue was extracted out with four 200 cc portions of n-hexane, and then residual n-hexane in the residue was distilled away under reduced pressure. Thus there was obtained 37 g of oily substance. It was confirmed by elemental analyses and $H^1$- and $P^{31}$-NMR that the oily substance is a compound of the following formula:

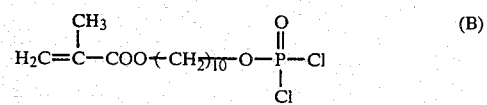

EXAMPLE 1

A two-pack primer of the following composition was prepared from the compound (B) synthesized in Production Example 2.

|  | Parts by weight |
| --- | --- |
| Formulation 1. | |
| 2,2-Bis[methacryloyloxy-polyethoxyphenyl]propane | 55 |
| Triethylene glycol dimethacrylate | 35 |
| Compound (B) | 10 |
| Benzoyl peroxide | 2 |
| Formulation 2. | |
| Ethanol | 100 |
| Sodium benzenesulfinate | 3 |
| N,N—diethanol-p-toluidine | 1 |

A specimen for adhesion was prepared by embedding a human molar in an epoxy resin in a cylindrical holder and then cutting the crown so that the dentin was exposed. On the other hand, a quadrangular prism of water-containing ivory measuring 10×10×30 mm was provided. The surface of the dentin and the end of the ivory prism were polished with #1000 sand paper. The polished surface of the dentin was covered with a piece of adhesive tape having a hole 5 mm in diameter. This hole establishes the area of adhesion. Formulation 1 and formulation 2 were mixed in equal quantities, and the mixture was applied to the dentin surface and the end of the ivory prism. Immediately, air was blown to the coated surface by using an air syringe to vaporize ethanol. A commercial dental composite "Clearfil-F" was mixed and the resulting paste was cast up on the end of the ivory prism. The ivory prism was pressed against the surface of the dentin, with the paste interposed between the two surfaces. After being kept pressed for 30 minutes, the dentin specimen and the ivory prism which had been bonded together were dipped in water at 37° C. for one day. Tensile bonding strength was measured. The bonding strength was 70 kg/cm$^2$ when failure occurred at the dentin-composite resin interface.

COMPARATIVE EXAMPLE 1

Example 1 was repeated except that the compound (B) was replaced by the compound (C) of the following formula which is described in Japanese Patent Laid-open No. 151607/1982.

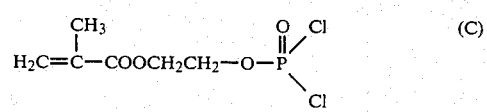

The tensile bonding strength was 4 kg/cm$^2$.

EXAMPLE 2

A powder-liquid type adhesive of the following composition was prepared from the compound (A) synthesized in Production Example 1.

|  | Parts by weight |
| --- | --- |
| Formulation 3. | |
| Methyl methacrylate | 97 |
| Compound (A) | 3 |
| Benzoyl peroxide | 2 |
| MEHQ | trace amount |
| Formulation 4. | |
| Polymethyl methacrylate powder | 100 |
| Sodium benzenesulfinate | 5 |
| N,N—diethanol-p-toluidine | 2 |

According to the method as described in Example 1, a specimen of dentin of a human tooth and an ivory prism were provided. Formulation 3 and formulation 4 were mixed in equal quantities. The resulting viscous slurry was applied to the dentin surface covered with a piece of adhesive tape having a hole 5 mm in diameter and to the end of the ivory prism. The dentin specimen and the ivory prism were pressed against each other. After being kept pressed for 30 minutes, they were dipped in water at 37° C. for one day. Tensile bonding strength was measured. The bonding strength was 62 kg/cm$^2$ when failure occurred at the dentin-resin interface.

COMPARATIVE EXAMPLE 2

Example 2 was repeated except that the compound (A) was replaced by the compound (D) of the following formula.

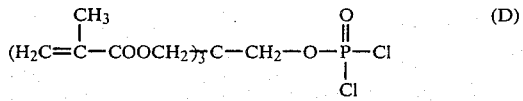

The tensile bonding strength to dentin measured according to the method of Example 2 was 13 kg/cm².

EXAMPLE 3

A powder-liquid type adhesive of the following composition was prepared from the compound (B) synthesized in Production Example 2.

|  | Parts by weight |
| --- | --- |
| Formulation 5. | |
| Methyl methacrylate | 97 |
| Compound (B) | 3 |
| Benzoyl peroxide | 2 |
| MEHQ | trace amount |
| Formulation 6. | |
| Polymethyl methacrylate powder | 100 |
| Sodium benzenesulfinate | 5 |
| N,N—diethanol-p-toluidine | 2 |

The resulting adhesive was evaluated with respect to adhesion to the dental Ni—Cr alloy (Ni: 92.7%, Cr: 6%, and others: 1.3%) and the dental porcelain (Vita VMK 68, No. 511P).

The Ni—Cr alloy was cast into a square plate measuring 4×10×10 mm. The porcelain specimen was also formed into a square plate measuring 4×10×10 mm. The 10×10 mm surfaces of the alloy plate and porcelain plate were polished with #1000 sand paper. The polished surface was used as the adherend. The adherend was covered with a piece of adhesive tape having a hole 5 mm in diameter. This hole establishes the area of bonding. On the other hand, a stainless steel round rod measuring 7 mm in diameter and 30 mm long was provided. The end of the rod was polished by sandblasting with alumina abrasive having an average particle diameter of 33 microns. Formulation 5 and formulation 6 were mixed in equal quantities. The resulting viscous paste was thickly applied to the end of the stainless steel rod. Immediately after application, the end of the stainless steel rod was pressed perpendicularly against the adherend of the Ni—Cr alloy specimen and the porcelain specimen. After adhesion, the specimens were dipped in water at 37° C. for 3 days. The tensile bonding strength was measured on an Instron tensile tester (at a crosshead speed of 2 mm/min).

In the case of Ni—Cr alloy, the cohesive failure of the adhesive occurred in all of ten specimens tested, and the average bonding strength was 275 kg/cm².

In the case of porcelain, both interfacial failure (at porcelain side) and cohesive failure occurred, and the average bonding strength was 146 kg/cm².

COMPARATIVE EXAMPLE 3

Formulation 7 was prepared according to the following composition, in which compound (E) has the following formula.

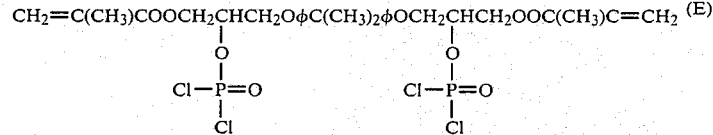

|  | Parts by weight |
| --- | --- |
| Formulation 7. | |
| Methyl methacrylate | 98 |
| Compound (E) | 2 |
| Benzoyl peroxide | 2 |
| MEHQ | trace amount |

Formulation 7 was combined with formulation 6 in Example 3 to give a powder-liquid type adhesive. The bonding test was carried out in the same manner as in Example 3. After dipping in water at 37° C. for 3 days, bonding strength was measured. The bonding strength for the Ni—Cr alloy specimen was 98 kg/cm² and that for the procelain specimen was 52 kg/cm².

EXAMPLE 4

A powder-liquid type adhesive of the following composition was prepared from the compound (B) synthesized in Production Example 2.

|  | Parts by weight |
| --- | --- |
| Formulation 8. | |
| 2,2-Bis[methacryloyloxypoly-ethoxyphenyl]propane | 60 |
| 1,6-Hexanediol dimethacrylate | 30 |
| compound (B) | 10 |
| Benzoyl peroxide | 2 |
| MEHQ | trace amount |
| Formulation 9. | |
| Silane-treated quartz powder | 100 |
| Sodium benzenesulfinate | 0.6 |
| N,N—diethanol-p-toluidine | 0.6 |

The resulting adhesive was evaluated with respect to adhesion of the dental Co—Cr alloy to a bovine tooth.

The Co—Cr alloy (Co: 62%, Cr: 32%, Mo: 3.5%, others: 2.5%) was cast into a round rod, 5 mm in diameter and 15 mm long. The end of the rod was polished by sandblasting. On the other hand, the enamel surface of the bovine tooth was polished with #1000 sand paper to make a flat surface on which to stand the above-mentioned round rod. The flat surface underwent acid etching with 40% aqueous solution of phosphoric acid. Formulation 8 and formulation 9 were mixed in a ratio of 1:3.5. The resulting pasty adhesive was applied to the end of the round rod of Co—Cr alloy. The end of the rod was pressed against the etched enamel surface. The superfluous paste which had been forced out was removed carefully. After being kept pressed for 1 hour, the specimens were dipped in water at 37° C. for 1 month. The bonding strength was measured on an Instron tensile tester. The average bonding strength of five specimens was 128 kg/cm². Failure occurred at the inerface between the adhesive and the enamel surface.

EXAMPLES 5 to 9

Adhesives were prepared in the same way as in Examples 1 and 3 from the compounds listed in Table 1. Their bonding strength for the dentin of human teeth, the Ni—Cr alloy, and the dental porcelain was measured as in Examples 1 and 3. The results are shown in Table 1.

which is described in Japanese Patent Laid-open No. 151607/1982. The resulting adhesive was evaluated in the same way as in Example 10. The tensile bonding strength for iron, aluminum, copper, α-alumina, and glass was lower than 50 kg/cm$^2$, and that for polymethyl methacrylate and polycarbonate was lower than 150 kg/cm$^2$.

TABLE 1

| Example No. | Compound | Bonding strength (kg/cm$^2$) | | |
|---|---|---|---|---|
| | | Human teeth | Ni—Cr alloy | Porcelain |
| 5 | $H_2C=C(CH_3)-COOCH_2-C_6H_4-CH_2O-P(=O)Cl_2$ | 65 | 230 | 108 |
| 6 | $H_2C=C(CH_3)-COOCH_2-C_6H_{10}(H)-CH_2O-P(=O)Cl_2$ | 66 | 196 | 102 |
| 7 | $H_2C=C(CH_3)-COOCH_2CH_2CH(CH_3)CH_2CH_2-O-P(=O)F_2$ | 60 | 173 | 84 |
| 8 | $H_2C=C(CH_3)-COOCH_2CH_2O-C_6H_4-CH_2CH_2-O-P(=O)Cl_2$ | 71 | 301 | 115 |
| 9 | $H_2C=C(CH_3)-COOCH_2CH(CH_2OOC(CH_2)_6CH_3)-O-P(=O)Cl_2$ | 55 | 207 | 92 |

EXAMPLE 10

As the adherends, round rods measuring 7 mm in diameter and 25 mm long were prepared from iron, aluminum, copper, α-alumina, glass, polymethyl methacrylate, and polycarbonate. The end of each rod was polished with #1000 silicon carbide sand paper.

Formulation 5 and formulation 6 in Example 3 were mixed in equal quantities. The resulting pasty adhesive was applied to the polished end of the rod, and two rods of the same kind were butted together. After 1 hour, the bonded specimens were dipped in water at room temperature for 1 week. The tensile bonding strength was measured. The results are as follows:

Iron: 332 kg/cm$^2$
Aluminum: 296 kg/cm$^2$
Copper: 218 kg/cm$^2$
α-Alumina: 235 kg/cm$^2$
Glass: 96 kg/cm$^2$
Polymethyl methacrylate: 191 kg/cm$^2$
Polycarbonate: 152 kg/cm$^2$

COMPARATIVE EXAMPLE 4

The same adhesive as in Example 3 was prepared except that the compound (B) in formulation 5 was replaced by a compound of the formula

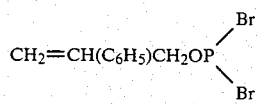

EXAMPLE 11

A cylindrical cavity measuring 4 mm in diameter and 4 mm deep was formed on the lingual surface of a human molar by using a diamond bur. The cavity was dried by using an air syringe. A mixture of equal quantities of formulation 1 and formulation 2 in Example 1 was applied to the entire cavity wall. Air was blown to the coated surface by using an air syringe to vaporize ethanol. A commercial dental composite resin "Clearfil-F" was filled in the cavity in the usual way. The tooth specimen was dipped in water at 37° C. for 1 day. Then, the tooth specimen was dipped in water at 4° C. and water at 60° C. alternately 100 times for 1 minute each. The water was colored with a dye. The tooth specimen was cut with a cutter to see if the dye had infiltrated into the interface between the tooth and the filling material. The infiltration of the dye was not found at all.

EXAMPLE 12

A conical cavity measuring 6 mm in diameter and 4 mm deep was formed on the occlusal surface of a human molar. An inlay that fits in the cavity was cast from type III gold alloy. A 1:3.5 mixture (by weight) of formulation 8 and formulation 9 in Example 4 was applied to the conical surface of the inlay. The inlay was forced into the cavity to effect bonding. After 30 minutes, the tooth specimen was dipped in water at 37° C. for 1 day. Then, the tooth specimen was subjected to thermal cycling test by dipping in water at 4° C. and water at 60° C. alternately. After the test, the inlay stayed in the cavity so firmly that it could not be pried off by a knife tip.

EXAMPLE 13

A 1-mm thick plate that fits to the lingual surface of a human anterior tooth was prepared by casting from an Ni—Cr alloy (Ni: 76%, Cr: 12%, Mo: 3%, others: 9%). The surface of the casting that comes into contact with the tooth was polished by sandblasting with 33-micron alumina abrasive. The lingual surface of the anterior tooth underwent acid etching for 1 minute with 40% aqueous solution of phosphoric acid.

A 1:3.5 mixture (by weight) of formulation 8 and formulation 9 in Example 4 was applied to the surface of the casting. The casting was bonded to the lingual surface of the anterior tooth. After 10 minutes, the bonded specimens were dipped in water at 37° C. for 1 day. The tensile bonding strength was 164 kg/cm². Interfacial failure occurred at the tooth surface.

EXAMPLE 14

A pit and fissure sealant for filling the fissure of a molar was prepared according to the following composition.

|  | Parts by weight |
| --- | --- |
| Formulation 10. | |
| 2,2-Bis(methacryloyloxypoly-ethoxyphenyl)propane | 60 |
| Neopentylglycol dimethacrylate | 30 |
| Compound (A) | 10 |
| Benzoyl peroxide | 2 |
| Formulation 11. | |
| Bis-GMA | 40 |
| HEMA | 40 |
| Neopentylglycol dimethacrylate | 20 |
| Sodium benzenesulfinate | 2 |
| N,N—diethanol-p-toluidine | 2 |

The fissure of a human molar was cleaned with an explorer, followed by washing and drying. The sealant (a 1:1 mixture of formulation 10 and formulation 11) was filled in the fissure without etching. Ten minutes after curing, the tooth specimen was dipped in water at 37° C. for 1 day. Then, the tooth specimen was dipped in water at 4° C. and water at 60° C. alternately 100 times for 1 minute each. The water was colored with a dye. The tooth specimen was cut with a cutter to see if the dye had infiltrated into the interface between the tooth and the filling material. The infiltration of the dye was hardly found.

EXAMPLE 15

A cylindrical cavity measuring 4 mm in diameter and 4 mm deep was formed on the buccal surface of a human molar by using a diamond bur. The cavity wall underwent acid etching for 1 minute with 40% aqueous solution of phosphoric acid, followed by washing and drying. The paste obtained by mixing formulation 8 and formulation 9 in Example 4 in the ratio of 1:3.5 by weight was filled in the cavity. Ten minutes after curing, the tooth specimen was dipped in water at 37° C. for 1 day. Then, the infiltration of dye into the bonding interface was examined in the same manner as in Example 4. The infiltration of the dye was hardly found.

What is claimed is:

1. An adhesive which comprises a polymerizable composition consisting of (a) 1 part by weight of a monomer represented by the formula

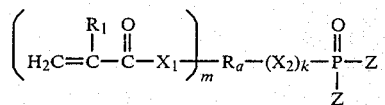

where $R_1$ denotes H or $CH_3$; $R_a$ denotes a $C_{6-40}$ organic residue having a valence of $m+1$; $X_1$ and $X_2$ denote O, S, or NR', (where R' denotes H or a $C_{1-6}$ hydrocarbon group), two of $X_1$ may be different from each other when m is 2; Z denotes a halogen; and m is 1 or 2 and k is 0 or 1, and (b) 0 to 199 parts by weight of a monomer selected from the group consisting of mono-, di-, tri-, and tetrafunctional (meth)acrylates, styrene, divinyl benzene, p-chlorostyrene, (meth)acrylamide or derivatives thereof, N-(hydroxymethyl)acrylamide, (meth)acrylic acid, isobutylvinyl ether, vinyl acetate, diethyl fumarate, diethyl maleate, maleic anhydride, methyl vinyl ketone, allyl chloride, vinyl naphthalene and vinylpyridine or combinations thereof.

2. An adhesive as set forth in claim 1, wherein m is 1.

3. An adhesive as set forth in claim 1, wherein m and k are 1, and $X_1$ and $X_2$ are —O—.

4. An adhesive as set forth in claim 3, wherein the $R_a$ is $-CH_2-_n$.

5. An adhesive as set forth in claim 3, wherein the $R_a$ is

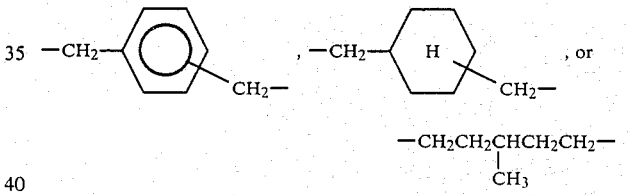

6. An adhesive as set forth in claim 3, wherein the $R_a$ is

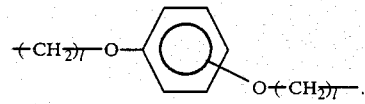

7. An adhesive as set forth in claim 3, wherein the $R_a$ is

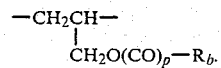

8. An adhesive as set forth in claim 1, wherein a curing agent is incorporated in an amount of 0.01 to 20 parts by weight for 100 parts by weight of the polymerizable monomers.

9. An adhesive as set forth in claim 8, wherein the curing agent is a redox type polymerization initiator.

10. An adhesive as set forth in claim 8, wherein the curing agent is a photosensitizer.

11. An adhesive as set forth in claim 1, wherein a volatile organic solvent having a boiling point lower than 150° C. at 760 Torr is incorporated in an amount of less than 300 times (by weight) the weight of the polymerizable monomers.

12. An adhesive as set forth in claim 1, wherein a filler is incorporated in an amount of 20 to 500 parts by weight for 100 parts by weight of the polymerizable monomers.

13. An adhesive as set forth in claim 1, wherein the vinyl monomer (b) is a mono-, di-, tri- or tetra-functional (meth)acrylate, styrene or derivatives thereof or vinyl acetate.

14. A method for restoring a decayed tooth which comprises applying an adhesive to the surface of the tooth cavity and subsequently filling the cavity with a dental filling material composed of a polymerizable monomer, filler and curing agent, said adhesive comprising
(a) 1 part by weight of a polymerizable monomer represented by the formula

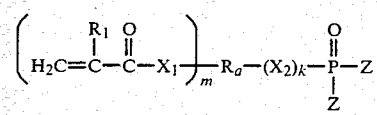

(where $R_1$ denotes H or $CH_3$; $R_a$ denotes a $C_{6-40}$ organic residue having a valence of $m+1$; $X_1$ and $X_2$ denote O, S, or NR', two of $X_1$ may be different from each other when m is 2; Z denotes a halogen; and m is 1 or 2 and k is 0 or 1),
(b) 0 to 199 parts by weight of monomer which is copolymerizable with said monomer (a), and
(c) 0.01 to 20 parts by weight of curing agent for 100 parts by weight of the polymerizable monomers.

15. A method as set forth in claim 14, wherein the adhesive is incorporated with a volatile organic solvent having a boiling point lower than 150° C. at 760 Torr in an amount of less than 300 times (by weight) the weight of the polymerizable monomers.

16. A method for restoring a decayed tooth which comprises filling an adhesive in the tooth cavity, said adhesive comprising
(a) 1 part by weight of a polymerizable monomer represented by the formula

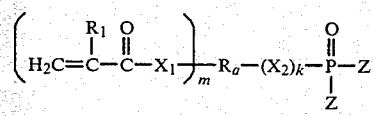

(where $R_1$ denotes H or $CH_3$; $R_a$ denotes a $C_{6-40}$ organic residue having a valence of $m+1$; $X_1$ and $X_2$ denote O, S, or NR', two of $X_1$ may be different from each other when m is 2; Z denotes a halogen; and m is 1 or 2 and k is 0 or 1),
(b) 0 to 199 parts by weight of monomer which is copolymerizable with said monomer (a),
(c) 20 to 500 parts by weight of filler for 100 parts by weight of the polymerizable monomers, and
(d) 0.01 to 20 parts by weight of curing agent for 100 parts by weight of the polymerizable monomers.

17. A method of dental treatment which comprises bonding a dental restorative material to teeth or bonding dental restorative materials to each other with an adhesive comprising
(a) 1 part by weight of a polymerizable monomer represented by the formula

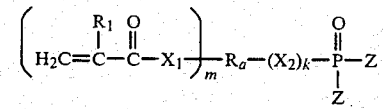

(where $R_1$ denotes H or $CH_3$; $R_a$ denotes a $C_{6-40}$ organic residue having a valence of $m+1$; $X_1$ and $X_2$ denote O, S, or NR', two of $X_1$ may be different from each other when m is 2; Z denotes a halogen; and m is 1 or 2 and k is 0 or 1),
(b) 0 to 199 parts by weight of monomer which is copolymerizable with said monomer (a),
(c) 20 to 500 parts by weight of filler for 100 parts by weight of the polymerizable monomers, and
(d) 0.01 to 20 parts by weight of curing agent for 100 parts by weight of the polymerizable monomers.

18. A method for preventing tooth decay which comprises coating the tooth surface with a composition which adheres to the tooth, said composition comprising
(a) 1 part by weight of a polymerizable monomer represented by the formula

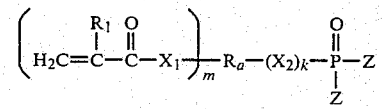

(where $R_1$ denotes H or $CH_3$; $R_a$ denotes a $C_{6-40}$ organic residue having a valence of $m+1$; $X_1$ and $X_2$ denote O, S, or NR', two of $X_1$ may be different from each other when m is 2; Z denotes a halogen; and m is 1 or 2 and k is 0 or 1),
(b) 0 to 199 parts by weight of monomer which is copolymerizable with said monomer (a), and
(c) 0.01 to 20 parts by weight of curing agent for 100 parts by weight of the polymerizable monomers.

* * * * *

UNITED STATES PATENT AND TRADEMARK OFFICE
CERTIFICATE OF CORRECTION

PATENT NO. : 4,515,930

DATED : May 7, 1985

INVENTOR(S) : Ikuo Omura et al

It is certified that error appears in the above-identified patent and that said Letters Patent is hereby corrected as shown below:

At Column 1, line 66, delete "PO(CH)$_2$" and insert therefor --PO(OH)$_2$--.

At Column 1, line 67, delete "P-O(OH)$_2$" and insert therefor --PO(OH)$_2$--.

At Column 2, line 48, delete "disulfonic" and insert therefor --phosphonic--.

At Column 3, line 60, delete "$+(H_2C=C(R_1)-C(=O)-X_1)_m$" and insert therefor -- $(H_2C=C(R_1)-C(=O)-X_1)_m$ --.

At Column 10, line 15, right-hand structure, delete "CH$_2$CH" and insert therefor --CH$_2$=CH--.

At Column 21, example No. 8 in Table 1, delete "CH$_2$CH$_2$-O-P" and insert therefor -- OCH$_2$CH$_2$-O-P --.

At Column 21, example No. 9 in Table 1, delete "P(=O)(Cl)(Cl)" and insert therefor -- P(=O)(Cl)-Cl --.

At Column 24, line 29, delete "-CH$_2{\overline{\overline{n}}}$" and insert therefor -- $+CH_2)_{\overline{n}}$ (where n is a natural number of 6 to 20)--.

UNITED STATES PATENT AND TRADEMARK OFFICE
CERTIFICATE OF CORRECTION

PATENT NO. : 4,515,930

DATED : May 7, 1985

INVENTOR(S) : Ikuo Omura et al

It is certified that error appears in the above-identified patent and that said Letters Patent is hereby corrected as shown below:

At Column 24, after the structure at line 45, insert --(where $\ell$ is 2, 3, or 4)--.

At Column 24, after the structure at line 55, insert --(where p is 0 or 1, and $R_b$ is a $C_{3-16}$ hydrocarbon group)--.

Signed and Sealed this

Sixteenth Day of September 1986

[SEAL]

Attest:

DONALD J. QUIGG

Attesting Officer

Commissioner of Patents and Trademarks